US012649754B2

(12) United States Patent
Ates et al.

(10) Patent No.: US 12,649,754 B2

(45) Date of Patent: Jun. 9, 2026

(54) PRODRUGS OF 2-(3,5-DICHLORO-1-METHYL-INDAZOL-4-YL)-1-[(1S,3R)-3-(HYDROXYMETHYL)-5-(1-HYDROXY-1-METHYL-ETHYL)-1-METHYL-3,4-DIHYDRO-1H-ISOQUINOLIN-2-YL] ETHANONE

(71) Applicant: UCB Biopharma SRL, Brussels (BE)

(72) Inventors: Ali Ates, Brussels (BE); Celal Ates, Brussels (BE); Laurent Provins, Brussels (BE)

(73) Assignee: UCB Biopharma SRL, Brussels (BE)

( * ) Notice: Subject to any disclaimer, the term of this patent is extended or adjusted under 35 U.S.C. 154(b) by 349 days.

(21) Appl. No.: 18/267,946

(22) PCT Filed: Dec. 16, 2021

(86) PCT No.: PCT/EP2021/086238

§ 371 (c)(1),
(2) Date: Jun. 16, 2023

(87) PCT Pub. No.: WO2022/129356

PCT Pub. Date: Jun. 23, 2022

(65) Prior Publication Data

US 2024/0083925 A1 Mar. 14, 2024

(30) Foreign Application Priority Data

Dec. 18, 2020 (EP) .................................... 20215254

(51) Int. Cl.
*C07D 401/06* (2006.01)
*C07F 9/6558* (2006.01)

(52) U.S. Cl.
CPC ........ *C07F 9/65583* (2013.01); *C07D 401/06* (2013.01)

(58) Field of Classification Search
CPC .......................... C07F 9/65583; C07D 401/06
See application file for complete search history.

(56) References Cited

U.S. PATENT DOCUMENTS 10,370,355 B2 * 8/2019 Ates ........................ A61P 25/16
2022/0259179 A1 8/2022 Ates et al.

FOREIGN PATENT DOCUMENTS

| | | |
|---|---|---|
| WO | 2013/066736 | 5/2013 |
| WO | WO2014/193781 | 12/2014 |
| WO | WO2016/055479 | 4/2016 |
| WO | WO2017/178377 | 10/2017 |
| WO | 2020/050722 | 3/2020 |
| WO | 2021001288 | 1/2021 |

OTHER PUBLICATIONS

Belles, Pharmacology Biochemistry and Behavior, vol. 222, 2023, 173506, 1-11. (Year: 2023).*
Luderman,, e17044, 1-13. Mol Pharmacol, 9:1197-1203, 2018. (Year: 2018).*
Liu, JD Insight, 2023, 8(16), e170434, 1-13. (Year: 2023).*
Lewis, J Pharmacol Exp Ther, 2015, 354: 340-349. (Year: 2015).*
Bundgaard, Design of Prodrugs, Elsevier, 1-27, 1985. (Year: 1985).*
International Search Report dated Jan. 28, 2022 for International Application No. PCT/EP2021/086238, 3 pages.
Meanwell (Top Med Chem, 2015, 9:283-382) (Year: 2015).
Hall et al. (J Med Chem, 2018, 62: 128-140) (Year: 2018).
Tian et al., J Pharm Pharmacol, 2010, 62:1534-1546 (Year: 2010).
Bajpai et al., IUCrJ, 2016, 3:490-439 (Year: 2016).
Kummerer, Klaus "Pharmaceuticals in the environment" Annual review of environment and resources (2010) vol. 35, pp. 57-75.
Wesserling, Martyna et al. "Will in vitro tests replace animal models in experimental oncology?", Journal of tissue science and engineering (2011) vol. 2(1), p. 102e. doi: 10.4172/2157-.
Szajewska, H. "Evidence-based medicine and clinical research: both are needed, neither is perfect", Annals of nutrition and metabolism (2018) vol. 72(3), pp. 13-23.
Brown (Bioisosteres in Medicinal Chemistry, 2012, Ch. 1) (Year: 2012).
Davoren et al. (J Med Chem, 2018, 61 :11384-11387 (Year: 2018).
Girmaw (Health Sci Rep, 2024, 7:e1984) (Year: 2024).
Blanchard et al. (Nat Rev Neural, 2022, 18:25-39) (Year: 2022).
Ke et al. (Aging and Disease, 2021, 12:223-246) (Year: 2021).
Davoren et al. (J Med Chem, 2018, 61 :11384-11397 (Year: 2018) (correction of citation in prior IDS).
Bajpai et al., IUCrJ, 2016, 3:430-439 (Year: 2016) (correction of citation in prior IDS).

* cited by examiner

*Primary Examiner* — D Margaret M Seaman
(74) *Attorney, Agent, or Firm* — McDonnell Boehnen Hulbert & Berghoff LLP

(57) ABSTRACT

The present invention relates to a prodrug of 2-(3,5-dichloro-1-methyl-indazol-4-yl)-1-[(1S,3R)-3-(hydroxymethyl)-5-(1-hydroxy-1-methyl-ethyl)-1-methyl-3,4-dihydro-1H-isoquinolin-2-yl]ethanone, which prodrug is represented by formula (II).

(II)

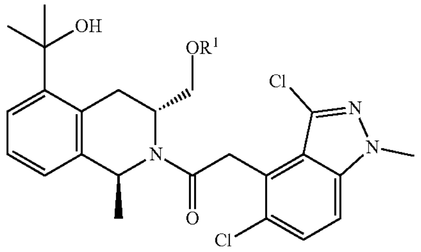

22 Claims, 2 Drawing Sheets

PRODRUGS OF 2-(3,5-DICHLORO-1-METHYL-INDAZOL-4-YL)-1-[(1S,3R)-3-(HYDROXYMETHYL)-5-(1-HYDROXY-1-METHYL-ETHYL)-1-METHYL-3,4-DIHYDRO-1H-ISOQUINOLIN-2-YL] ETHANONE

CROSS-REFERENCE TO RELATED APPLICATIONS

This application is a U.S. national phase of International Application No. PCT/EP2021/086238, filed Dec. 16, 2021, which claims priority from European Patent Application No. 20215254.2, filed Dec. 18, 2020, the disclosure of each of which is hereby incorporated by reference in its entirety.

FIELD OF THE INVENTION

This invention relates to prodrugs of 2-(3,5-dichloro-1-methyl-indazol-4-yl)-1-[(1S,3R)-3-(hydroxymethyl)-5-(1-hydroxy-1-methyl-ethyl)-1-methyl-3,4-dihydro-1H-isoquinolin-2-yl]ethanone.

This invention also relates to processes for the preparation of these prodrugs and to pharmaceutical compositions including such prodrugs.

BACKGROUND OF THE INVENTION

International patent application no. PCT/EP2020/068183, published as WO2021/001288, discloses 2-(3,5-dichloro-1-methyl-indazol-4-yl)-1-[(1S,3R)-3-(hydroxymethyl)-5-(1-hydroxy-1-methyl-ethyl)-1-methyl-3,4-dihydro-1H-isoquinolin-2-yl]ethanone of formula (I), (I)

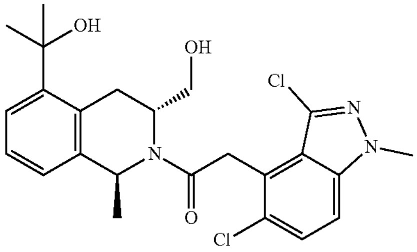

which compound acts as a D1 Positive Allosteric Modulator and is accordingly of benefit as a pharmaceutical agent for the treatment of diseases in which D1 receptors play a role.

International patent application no. PCT/EP2020/068183, published as WO2021/001288, further discloses that compound of formula (I) may be useful in the treatment and/or prevention of cognitive and negative symptoms in schizophrenia, cognitive impairment related to neuroleptic therapy, Mild Cognitive impairment (MCI), impulsivity, Attention-Deficit Hyperactivity Disorder (ADHD), Parkinson's disease and other movement disorders, dystonia, Parkinson's dementia, Huntington's disease, dementia with Lewy Body, Alzheimer's disease drug addiction, sleep disorders, apathy, traumatic spinal cord injury or neuropathic pain.

It is therefore desirable to develop formulations of compound of formula (I) that will be suitable for administration to patients suffering from any one of the above-mentioned disease.

In particular, Example 2.8. of international patent application no. PCT/EP2020/068183, published as WO2021/001288, discloses inter alia the monohydrated crystalline form of 2-(3,5-dichloro-1-methyl-indazol-4-yl)-1-[(1S,3R)-3-(hydroxymethyl)-5-(1-hydroxy-1-methyl-ethyl)-1-methyl-3,4-dihydro-1H-isoquinolin-2-yl]ethanone.

This monohydrated crystalline form of 2-(3,5-dichloro-1-methyl-indazol-4-yl)-1-[(1S,3R)-3-(hydroxymethyl)-5-(1-hydroxy-1-methyl-ethyl)-1-methyl-3,4-dihydro-1H-isoquinolin-2-yl]ethanone has limited solubility which may result in difficulties to formulate it and/or low biovailability, if an oral administration is desired.

There is therefore a need to improve the solubility of the monohydrated crystalline form of 2-(3,5-dichloro-1-methyl-indazol-4-yl)-1-[(1S,3R)-3-(hydroxymethyl)-5-(1-hydroxy-1-methyl-ethyl)-1-methyl-3,4-dihydro-1H-isoquinolin-2-yl] ethanone so that it can be incorporated in a pharmaceutical composition, in particular for oral administration.

SUMMARY OF THE INVENTION

The present invention provides prodrugs of 2-(3,5-dichloro-1-methyl-indazol-4-yl)-1-[(1S,3R)-3-(hydroxymethyl)-5-(1-hydroxy-1-methyl-ethyl)-1-methyl-3,4-dihydro-1H-isoquinolin-2-yl]ethanone, which prodrugs are represented by formula (II), or pharmaceutically acceptable salts thereof, (II)

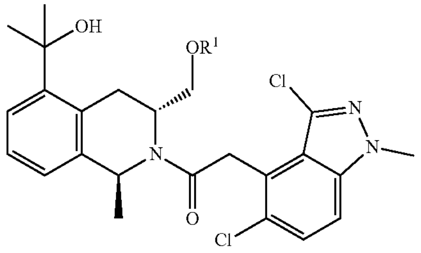

wherein $R^1$ represents —P(═O)(OH)$_2$, —P(═O)(OM$^1$)$_2$, —P(═O)(O$^-$)$_2$M$^2$ or —C(═O)R$^a$;

$R^a$ represents a $C_{1-6}$ alkyl substituted by amino;

$M^1$ represents a monovalent cation; and $M^2$ represents a divalent cation.

In a further aspect, the present invention therefore provides a pharmaceutical composition comprising a prodrug of formula (II), and a pharmaceutically acceptable carrier.

International patent application no. PCT/EP2020/068183, published as WO2021/001288, discloses that compound of formula (I) acts as a D1 Positive Allosteric Modulator and is accordingly of benefit as a pharmaceutical agent for the treatment of diseases in which D1 receptors play a role.

International patent application no. PCT/EP2020/068183, published as WO2021/001288, further discloses that compound of formula (I) may be useful in the treatment and/or prevention of cognitive and negative symptoms in schizophrenia, cognitive impairment related to neuroleptic therapy, Mild Cognitive impairment (MCI), impulsivity, Attention-Deficit Hyperactivity Disorder (ADHD), Parkinson's disease and other movement disorders, dystonia, Parkinson's dementia, Huntington's disease, dementia with Lewy Body, Alzheimer's disease, drug addiction, sleep disorders, apathy, traumatic spinal cord injury or neuropathic pain.

Therefore, in a further aspect, the present invention provides prodrugs of formula (II), or pharmaceutical composition thereof, for use in the treatment and/or prevention of cognitive and negative symptoms in schizophrenia, cognitive impairment related to neuroleptic therapy, Mild Cognitive impairment (MCI), impulsivity, Attention-Deficit Hyperactivity Disorder (ADHD), Parkinson's disease and other movement disorders, dystonia, Parkinson's dementia, Huntington's disease, dementia with Lewy Body, Alzheimer's disease, drug addiction, sleep disorders, apathy, traumatic spinal cord injury or neuropathic pain.

DETAILED DESCRIPTION OF THE INVENTION

Figure 1:
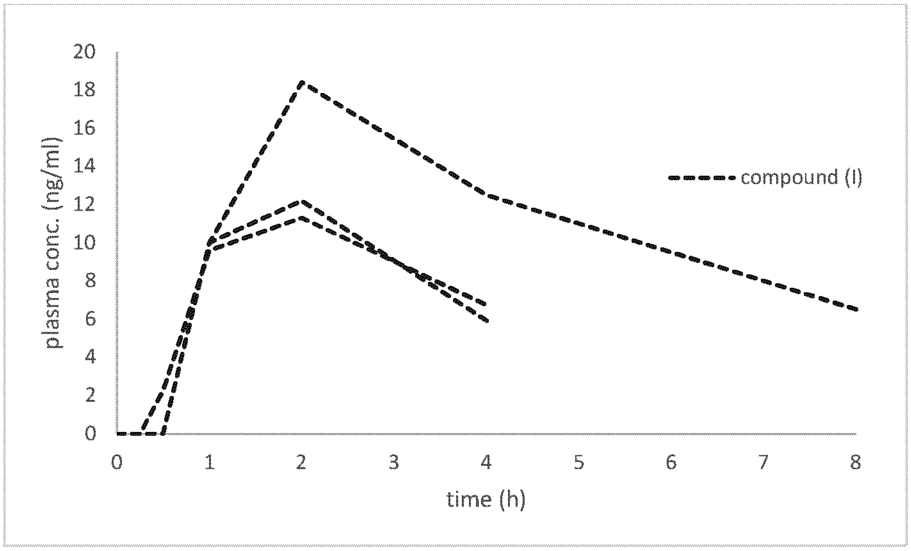
FIG. 1 represents a graph of the concentration of compound (I) in the plasma of three different animals plotted in function of time after administration of a suspension of prodrug (II-A) prepared according to Example 7 as further described herein.

The term "prodrug" as used herein, when referring to prodrugs of compound of formula (I), means a functional derivative of compound of formula (I) which is readily convertible in vivo into the required compound of formula (I). Prodrugs of compound of formula (I) according to the present invention are represented by compound of formula (II) as generally defined here above and as further described herein.

The term "$C_{1-6}$ alkyl" as used herein refers to aliphatic hydrocarbon groups which may be straight or branched and may comprise 1 to 6 carbon atoms in the chain. Suitable alkyl groups which may be present on the compounds of use in the invention include straight-chained and branched $C_{1-4}$ alkyl groups. Illustrative $C_{1-6}$ alkyl groups include methyl, ethyl, propyl and butyl.

In a first embodiment according to the present invention, $R^1$ represents —P(═O)$(OH)_2$. In a second embodiment according to the present invention, $R^1$ represents —P(═O)$(OM^1)_2$. In a third embodiment according to the present invention, $R^1$ represents —P(═O)$(O^-)_2M^2$. In a fourth embodiment according to the present invention, $R^1$ represents C(=O)$R^a$.

Generally, $M^1$ represents an alkali metal cation. Suitable examples of alkali metal cations are $Na^+$ and $K^+$.

Generally, $M^2$ represents an alkali earth metal cation. A suitable example of alkali earth metal cation is $Ca^{++}$.

Generally, $R^a$ represents a $C_{1-6}$ alkyl substituted by amino. In a first embodiment, $R^a$ represents (amino)butyl. In a second embodiment, $R^a$ represents (amino)pentyl.

Illustrative examples of compounds of formula (II) according to the present invention are represented by compound of formula (II-A), (II-B) and (II-C).

(II-A)

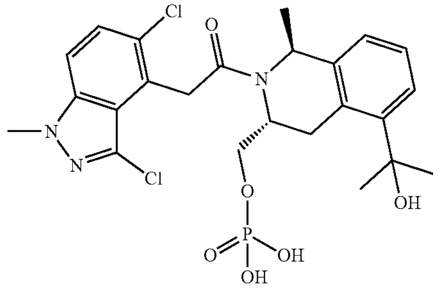

(II-B)

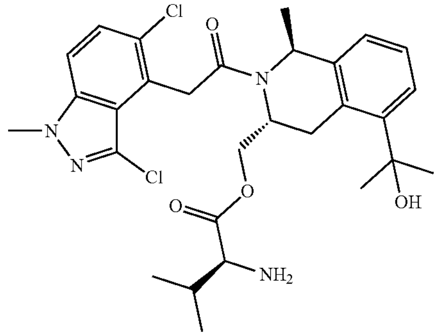

(II-C)

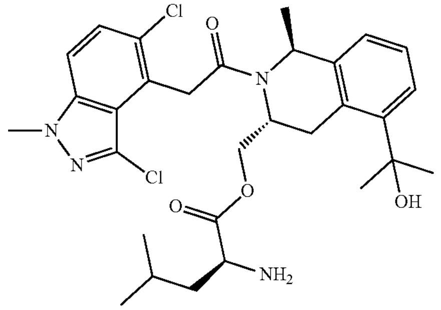

In a first embodiment, the present inventions relates to a prodrug of formula (II-A).

In a second embodiment, the present inventions relates to a prodrug of formula (II-B).

In a third embodiment, the present invention relates to a prodrug of formula (II-C).

In a fourth embodiment, the present invention relates to salts of compounds of formula (II-A). In one aspect of this embodiment, the present invention relates to the disodium salt of compound of formula (II-A) which corresponds to compound of formula (II) wherein $R^1$ represents —P(═O)$(OM^1)_2$ and $M^1$ represents $Na^+$.

In another aspect of this embodiment, the present invention relates to the calcium salt of compound of formula (II-A) which corresponds to compound of formula (II) wherein $R^1$ represents P(═O)$(O^-)_2M^2$ and $M^2$ represents $Ca^{++}$.

The prodrugs represented by formula (II), according to the present invention, are generally more soluble than the crystalline form of the monohydrate of compound of formula (I), herein referred to as compound of formula (Ia). Such improved solubility is particularly advantageous when a pharmaceutical composition needs to be prepared, in particular for oral administration, because a higher bioavailability may be achieved. This may also allow reduction of the dose and hence the tablet size to be used when a solid formulation is desired.

Table 1 of the Examples shows comparative solubility data between compound of formula (II) and compound formula (Ia) obtained according to the present Examples showing a minimum 20-fold increase, irrespective of the media used.

The prodrugs according to the present invention may be additionally combined with pharmaceutically acceptable excipients such as diluents, binders, disintegrants, lubricants, glidants or carrier to form a suitable pharmaceutical composition.

To prepare such a pharmaceutical composition, prodrugs according to the present invention, is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, parenteral or intranasal.

Pharmaceutical compositions suitable for oral administration can be solids or liquids and can, for example, be in the form of tablets, pills, dragees, gelatin capsules, solutions, syrups, chewing-gums and the like.

To this end, the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as croscarmellose sodium or crospovidone alginic acid, a lubricant such as magnesium stearate, a glidant such as colloidal silicon dioxide, a sweetener such as sucrose or saccharin, or colouring agents or a flavouring agent such as peppermint or methyl salicylate and coating agents such as Opadry® (I, II, AMB II, QX or EZ).

The invention also contemplates compositions which can release the active substance in a controlled manner. Pharmaceutical compositions which can be used for parenteral administration are in conventional form such as aqueous or oily solutions or suspensions generally contained in ampoules, disposable syringes, glass or plastics vials or infusion containers.

In addition to the prodrugs, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose, and viscosifying agents such as methylcellulose, Hydroxypropylcellulose (HPC-SSL), hypromellose (HPMC) and finally stabilizing agents such as TWEEN® 80, PVPVA, PVP, and PVA.

These pharmaceutical forms are prepared using methods which are routinely used by pharmacists.

The amount of prodrugs of formula (II) according to the present invention in the pharmaceutical compositions can fall within a wide range of concentrations and depends on a variety of factors such as the patient's sex, age, weight and medical condition, as well as on the method of administration. Thus, the quantity of prodrugs for oral administration is generally comprised between about 0.5% by weight and about 80% by weight with respect to the total weight of the composition, suitably between about 20% and about 60% by weight with respect to the total weight of the composition.

International patent application no. PCT/EP2020/068183, published as WO2021/001288, describes that compound of formula (I) may be useful for the treatment of diseases and/or disorders in which D1 receptors play a role, and in particular cognitive and negative symptoms in schizophrenia, cognitive impairment related to neuroleptic therapy, Mild Cognitive impairment (MCI), impulsivity, Attention-Deficit Hyperactivity Disorder (ADHD), Parkinson's disease and other movement disorders, dystonia, Parkinson's dementia, Huntington's disease, dementia with Lewy Body, Alzheimer's disease, drug addiction, sleep disorders, apathy, traumatic spinal cord injury or neuropathic pain.

Thus in a further aspect, the present invention provides for prodrugs of formula (II) as described herein, or pharmaceutical composition thereof, for use in the treatment and/or prevention of cognitive and negative symptoms in schizophrenia, cognitive impairment related to neuroleptic therapy, Mild Cognitive impairment (MCI), impulsivity, Attention-Deficit Hyperactivity Disorder (ADHD), Parkinson's disease and other movement disorders, dystonia, Parkinson's dementia, Huntington's disease, dementia with Lewy Body, Alzheimer's disease, drug addiction, sleep disorders, apathy, traumatic spinal cord injury or neuropathic pain.

In a particular aspect, the present invention provides for prodrugs of formula (II) according to the present invention, or pharmaceutical compositions thereof, for use in the treatment of Parkinson's disease and other movement disorders, Alzheimer's disease, or cognitive and negative symptoms in schizophrenia.

Compound of formula (I) may be prepared by a process involving reacting an intermediate of formula (A) with an intermediate of formula (B), (A)

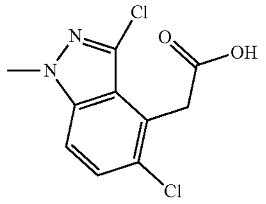

(B)

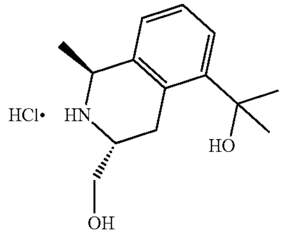

Intermediate (B) may be conveniently reacted with intermediate of formula (A) in the presence of (2-(1H-benzotriazol-1-yl)-1,1,3,3-tetramethyluronium hexafluorophosphate (HBTU) or another coupling agent known to the person skilled in the art, in a suitable solvent, e.g. dimethylformamide, with an excess amount of a base, e.g. N,N-diisopropylethylamine.

Intermediate of formula (B) may be prepared by a process involving reaction of intermediates of formula (IV), (IV)

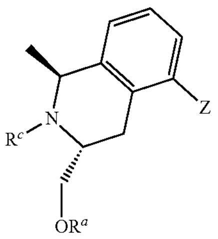

wherein

Z represents halogen or 1-hydroxy-1-methyl ethyl;

$R^a$ represents tert-butyl dimethylsilyl; and $R^c$ represents hydrogen or tert-butoxycarbonyl.

In a first step, intermediate of formula (IV), wherein Z represents bromo, and $R^c$ represents hydrogen, herein after referred to as intermediate (IVa), may be protected with an appropriate protective group, according to methods known to the skilled in the art to afford a compound of formula (IV), wherein Z represents bromo and $R^c$ represents tert-butoxycarbonyl, herein after referred to as intermediate (IVb).

In a second step, a metal-halogen exchange reaction may be performed e.g. in the presence of n-BuLi, in a suitable solvent, e.g. tetrahydrofuran, at low temperature, in the presence of dry acetone under continuous flow, according to a method described in the accompanying Examples, to afford corresponding intermediate (IV) as described above wherein Z represents 1-hydroxy-1-methyl ethyl, herein after referred to as intermediate (IVc).

The tert-butoxycarbonyl (Boc) group ($R^c$) may then first be deprotected according to methods known to the person skilled in the art or as further described in the accompanying Examples, followed by deprotection of the trimethylsilyl group formed during Boc group deprotection and the tert-butyl dimethylsilyl group ($R^a$) to afford intermediate (B).

Intermediate of formula (IVa) may be prepared by a process involving reaction of an intermediate of formula (V), wherein Y is a halogen, e.g. bromo, and $R^a$ is defined above for intermediate of formula (IV).

(V)

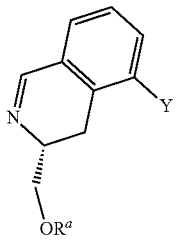

The reaction is conveniently effected in the presence of methyl magnesium chloride, in a suitable solvent e.g. tetrahydrofuran, at low temperature.

Intermediate (V) may be prepared by a two-steps process involving reaction of intermediate of formula (VI), (VI)

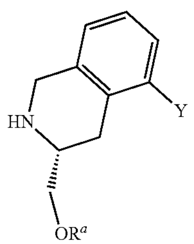

wherein Y is as defined above for intermediate of formula (V) and $R^a$ represents hydrogen or tert-butyl-dimethylsilyl.

In a first step intermediate (VI) wherein $R^a$ represents hydrogen is reacted with tert-butyldimethylsilyl chloride in the presence of a suitable base e.g. 4-dimethylamino-pyridine at room temperature, to afford intermediate (VI) wherein $R^a$ represents tert-butyl-dimethylsilyl.

In a second step, intermediate (VI) wherein $R^a$ represents tert-butyl-dimethylsilyl is reacted with N-Chlorosuccinimide (NCS), in a suitable solvent, e.g. THF to afford intermediate (V).

Intermediate (VI) wherein $R^a$ represents hydrogen may be prepared by a process involving intermediate of formula (VII), wherein Y is as defined above for intermediate (V).

(VII)

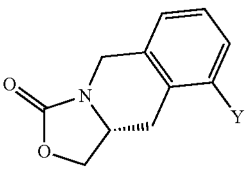

The reaction is conveniently effected in the presence of a strong base, e.g. sodium hydroxide, in a suitable solvent, e.g. mixture of ethanol and water, at high temperature.

Intermediate of formula (VII) may be prepared by a process involving reaction of intermediate (VIII), (VIII)

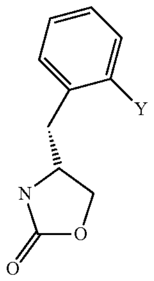

wherein Y is as defined here above for intermediate of formula (V).

The reaction is conveniently effected in the presence of trimethylsilyltriflate and paraformaldehyde, in a suitable solvent e.g. dichloromethane.

Intermediate (VIII) may be prepared by a two-steps process involving commercially available intermediate (IX), (IX)

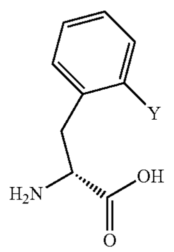

wherein Y is as defined above for intermediate (V).

The reaction is conveniently effected according to the methods described in the accompanying examples or according to methods known to the person skilled in the art.

Intermediate of formula (A) may be prepared by a multi-step process involving reaction of intermediates of formula (X), (X)

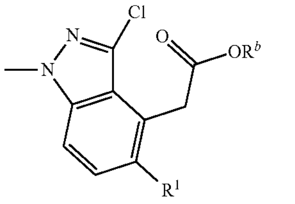

wherein $R^1$ represents chloro, amino or nitro; and $R^b$ represents hydrogen or tert-butyl.

In a first step, intermediate of formula (X) wherein $R^1$ represents nitro and $R^b$ represents tert-butyl, herein after referred to as intermediate (Xa), is reduced into the corresponding intermediate (X) wherein $R^1$ represents amino and $R^b$ represents tert-butyl, herein after referred to as intermediate (Xb).The reaction is conveniently effected by Pd/C catalyzed hydrogenation under high pressure, in a suitable solvent e.g. methanol.

Intermediate (Xb) is transformed into corresponding intermediate (X) wherein $R^1$ represents chloro and $R^b$ represents hydrogen, herein after referred to as intermediate (Xc), by adding concentrated hydrochloric acid and sodium nitrite, followed by further addition of hydrochloric acid and copper chloride (II). The reaction is conveniently effected at low temperature.

Intermediate (A) may then obtained directly from intermediate (Xc) by reaction with N-chlorosuccinimide according to the methods describe in the accompanying Examples or according to methods known to the person skilled in the art.

Intermediate of formula (Xa) may be prepared by a process involving an intermediate of formula (XI), (XI)

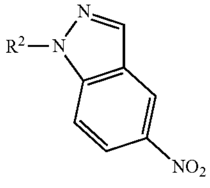

wherein $R^2$ represents hydrogen or methyl.

In a first step commercially available intermediate of formula (XI) wherein $R^2$ represents hydrogen, herein after referred to as intermediate (XIa), is reacted with methyl iodide in the presence of a strong base, e.g. potassium hydroxide, in a suitable solvent, e.g. dimethylformamide. The resulting intermediate (XI) wherein $R^2$ represents methyl, herein after referred to as intermediate (XIb) is then reacted with tert-butyl 2-chloroacetate in the presence of potassium tert-butoxide, in a suitable solvent, e.g. tetrahydrofuran, at low temperature, to afford intermediate (Xa).

Prodrugs of formula (II) may be obtained by functional group transformation of compound of formula (I).

Compounds of formula (II) wherein $R^1$ represents $—P(=O)(OH)_2$ are prepared according to the procedure further described in Example 3 or any other method known to the person skilled in the art.

Compounds of formula (II) wherein $R^1$ represents $—P(=O)(OM^1)_2$ or $—P(=O)(O^-)_2M^2$ may be obtained from compounds of formula (II) wherein $R^1$ represents $—P(=O)(OH)_2$ by reaction with a base according to methods conventional to the skilled person in the art.

Compounds of formula (II) wherein $R^1$ represents $C(=O)R^a$; and $R^a$ represents a $C_{1-6}$ alkyl substituted by amino, are typically prepared in a two-step procedure from compound of formula (I).

(i) Compound of formula (I) is reacted with the corresponding carboxylic acid of the $C_{1-6}$ alkyl substituted by amino, in which the amino group is protected by a suitable protecting group. Such carboxylic acid is generally commercially available.

The reaction is conveniently effected at room temperature in a suitable solvent such as dichloromethane.

(ii) Protecting group of the amino group of the compound obtained as a result of step (i) is removed according to conventional method known to the person skilled in the art, for example by reaction with an acid.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention. Alternatively the non desired enantiomer may be racemized into the desired enantiomer, in the presence of an acid or a base, according to methods known to the person skilled in the art, or according to methods described in the accompanying Examples.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 3rd edition, 1999. The protecting groups may be removed at any convenient subsequent stage utilising methods known from the art.

EXAMPLES

Abbreviations/Recurrent Reagents

Ac: Acetyl
ACN: Acetonitrile
Brine: Saturated aqueous sodium chloride solution
nBu: n-butyl
tBu: tert-butyl
CV: column volumes
DCC: Dicyclohexylcarbodiimide
DCM: Dichloromethane
DMAP: 4-Dimethylaminopyridine
DMF: N,N-Dimethylformamide
DMSO: Dimethylsulfoxide
$ES^+$: Electrospray Positive Ionisation
Et: Ethyl
EtOH: Ethanol
$Et_2O$: Diethyl ether
EtOAc: Ethyl acetate
h: Hour
HPLC: High Performance Liquid Chromatography
IPAC: Isopropyl acetate
LC: Liquid Chromatography
LCMS: Liquid Chromatography Mass Spectrometry
Me: Methyl
MeOH: Methanol
min.: minutes
NCS: N-Chlorosuccinimide
NMR: Nuclear magnetic resonance
iPr: isopropyl
iPrOH: isopropanol
p-TSA: p-toluenesulfonic acid
rt: room temperature
RT: Retention Time
SFC: Supercritical Fluid Chromatography
SPE: Solid phase extraction
t-BuOK: Potassium tert-butoxide
TBS: tert-Butyldimethylsilyl
TEA: Triethylamine
TFA: Trifluoroacetic acid
THF: Tetrahydrofuran
TLC: Thin Layer Chromatography
TMS: Trimethylsilyl
UPLC: Ultra High Performance Liquid Chromatography IUPAC names have been generated using Biovia Draw Version 19.1 (2019) and 20.1 (2020).

1. Analytical Methods

All reactions involving air or moisture-sensitive reagents were performed under a nitrogen or argon atmosphere using dried solvents and glassware. Experiments requiring microwave irradiation are performed on a Biotage Initiator Sixty microwave oven upgraded with version 2.0 of the operating software. Experiments are run to reach the required temperature as quickly as possible (maximum irradiation power: 400 W, no external cooling). Commercial solvents and reagents were generally used without further purification, including anhydrous solvents when appropriate (generally Sure-Seal™ products from Aldrich Chemical Company or AcroSeal™ from ACROS Organics). In general reactions were followed by thin layer chromatography, HPLC or mass spectrometry analyses.

Mass spectrometric measurements in LCMS mode are performed using different methods and instrument as follows:

Basic LCMS Method 1:

A QDA Waters simple quadrupole mass spectrometer is used for LCMS analysis. This spectrometer is equipped with an ESI source and an UPLC Acquity Classic with diode array detector (210 to 400 nm). Data is acquired in a full MS scan from m/z 70 to 800 in positive/negative modes with a basic elution. The reverse phase separation is carried out at 45° C. on a Waters Acquity UPLC BEH C18 1.7 μm (2.1×50 mm) column for basic elution. Gradient elution is done with $H_2O$/ACN/ammonium formate (95/5/63 mg/L)+100 μL/L $NH_4OH$ (solvent A) and ACN/$H_2O$/ammonium formate (95/5/63 mg/L)+100 μL/L $NH_4OH$ (solvent B). Injection volume: 1 μL. Full flow in MS.

| Time (min) | A (%) | B (%) | Flow (mL/min) |
|---|---|---|---|
| 0 | 99 | 1 | 0.8 |
| 0.15 | 99 | 1 | 0.8 |
| 1.6 | 5 | 95 | 0.8 |
| 1.65 | 5 | 95 | 0.8 |
| 2 | 5 | 95 | 0.8 |
| 2.05 | 99 | 1 | 0.8 |
| 2.75 | 99 | 1 | 0.8 |

Some reaction mixtures could be treated using Isolute® separator phase cartridges (from Biotage), acidic columns or catch and release SPE (Solid Phase Extraction) cartridges. Crude materials could be purified by normal phase chromatography, preparative TLC, (acidic or basic) reverse phase chromatography, chiral separation trituration or recrystallization.

Normal phase chromatography was performed using silica gel columns (100:200 mesh silica gel or cartridges for normal phase column chromatography systems such as Isolera™ Four from Biotage® or Teledyne Isco CombiNormal phase column®).

Products were generally dried under vacuum before final analyses and submission to biological testing.

NMR spectra were recorded on a BRUKER AVANCEIII 400 MHz-Ultrashield NMR Spectrometer fitted with a Windows 7 Professional workstation running Topspin 3.2 software and a 5 mm Double Resonance Broadband Probe (PABBI $^1H/^{19}F$-BB Z-GRD Z82021/0075) or a 1 mm Triple Resonance Probe (PATXI $^1H/D$-$^{13}C/^{15}N$ Z-GRD Z868301/004).

Chemical shifts are referenced to signals deriving from residual protons of the deuterated solvents (DMSO-$d_6$, MeOH-$d_4$ or $CDCl_3$). Chemical shifts are given in parts per million (ppm) and coupling constants (J) in Hertz (Hz). Spin multiplicities are given as broad (br), singlet (s), doublet (d), triplet (t), quartet (q) and multiplet (m).

All final products were analysed by LCMS in both basic and acid modes, as follows:

Basic LCMS Method 2:

A QDA Waters simple quadrupole mass spectrometer is used for LCMS analysis. This spectrometer is equipped with an ESI source and an UPLC Acquity Classic with diode array detector (210 to 400 nm). Data is acquired in a full MS scan from m/z 70 to 800 in positive/negative modes with a basic elution. The reverse phase separation is carried out at 45° C. on a Waters Acquity UPLC BEH C18 1.7 μm (2.1×100 mm) column for basic elution. Gradient elution is done with $H_2O$/ACN/ammonium formate (95/5/63 mg/L)+100 μL/L $NH_4OH$ (solvent A) and ACN/H 2 0/ammonium formate (95/5/63 mg/L)+100 μL/L $NH_4OH$ (solvent B). Injection volume: 1 μL. Full flow in MS.

| Time (min) | A (%) | B (%) | Flow (mL/min) |
|---|---|---|---|
| 0 | 99 | 1 | 0.4 |
| 0.8 | 99 | 1 | 0.4 |
| 5.30 | 0 | 100 | 0.4 |
| 5.35 | 0 | 100 | 0.5 |
| 7.30 | 0 | 100 | 0.5 |
| 7.35 | 99 | 1 | 0.4 |
| 9 | 90 | 1 | 0.4 |

Acid LCMS Method:

A QDA Waters simple quadrupole mass spectrometer is used for LCMS analysis. This spectrometer is equipped with an ESI source and an UPLC Acquity Hclass with diode array detector (210 to 400 nm). Data are acquired in a full MS scan from m/z 70 to 800 in positive/negative modes with an acidic elution. The reverse phase separation is carried out at 45° C. on a Waters Acquity UPLC HSS T3 1.8 μm (2.1×100 mm) column for acidic elution. Gradient elution is done with $H_2O$/ACN/TFA (95/5/0.05%) (solvent A) and ACN (solvent B).

| Time (min) | A (%) | B (%) | Flow (mL/min) |
|---|---|---|---|
| 0 | 99 | 1 | 0.4 |
| 0.8 | 99 | 1 | 0.4 |
| 5.3 | 5 | 95 | 0.4 |

-continued

| Time (min) | A (%) | B (%) | Flow (mL/min) |
|---|---|---|---|
| 5.35 | 5 | 95 | 0.5 |
| 7.3 | 5 | 95 | 0.5 |
| 7.35 | 99 | 1 | 0.4 |
| 9 | 99 | 1 | 0.4 |

2. Preparation of Monohydrated Crystalline Form of 2-(3,5-dichloro-1-methyl-indazol-4-yl)-1-[(1S, 3R)-3-(hydroxymethyl)-5-(1-hydroxy-1-methyl-ethyl)-1-methyl-3,4-dihydro-1H-isoquinolin-2-yl] ethanone (Ia)

Compound of formula (Ia) was prepared by applying the same synthetic method described in Example 2 of co-pending international patent application WO 2021/001288, herein incorporated by reference.

The following recristallization protocol was also applied as an alternative to the recristallization protocol disclosed in section 2.8:

A recristallization is carried out on 5.00 g Crude material is solubilized in 240 ml of dimethylsulfoxide. The solution is heated to 40° C. then filtered on a P3 sintered glass. The reactor and filter are rinsed with 35 ml dimethylsulfoxide. The filtrate is transferred to a clean reactor and heated to 85° C. 110 ml of water are dosed slowly over 30 minutes. 250 mg of compound (Ia) (0.5% w/w, monohydrate form) are then added to the reaction mixture. The mixture is stirred for 2 h 30 at 85° C. while crystalline material comes out of solution before being cooled down slowly to 20° C. over 12 hours. The suspension is filtered and the filtercake is rinsed successively with several portions of water and then with 150 ml of ethyl acetate. The filtercake is dried under vacuum at 50-60° C. Compound (Ia) is obtained as 46.9 g of an off-white powder. Yield=94%

$^1H$ NMR (400 MHz, DMSO-$d_6$) δ 7.65 (dd, J=9.0, 2.2 Hz, 1H), 7.52 (dd, J=9.0, 2.1 Hz, 1H), 7.37 (ddd, J=19.6, 7.6, 1.7 Hz, 1H), 7.25-7.03 (m, 2H), 5.30 (q, J=6.5 Hz, 0.3H), 5.16-4.99 (m, 1.7H), 4.99-4.84 (m, 0.7H), 4.63-4.30 (m, 3.3H), 4.17-3.93 (m, 4H), 3.28 (dt, J=10.5, 5.1 Hz, 1.3H), 3.10-2.85 (m, 1.7H), 1.56 (dd, J=13.2, 6.9 Hz, 6.7H), 1.24 (d, J=6.5 Hz, 2.3H).

3. Preparation of Compound of Formula (II-A)—[(1S,3R)-2-[2-(3,5-dichloro-1-methyl-indazol-4-yl) acetyl]-5-(1-hydroxy-1-methyl-ethyl)-1-methyl-3,4-dihydro-1H-isoquinolin-3-yl]methyl Dihydrogen Phosphate and its Disodium (II-A-Na) and Calcium (II-A-Ca) Salts

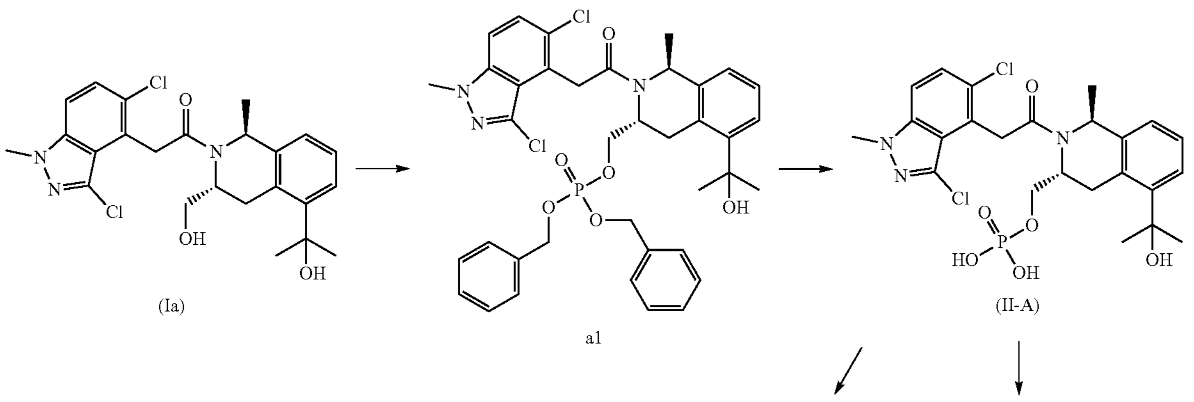

(Ia) a1 (II-A)

-continued

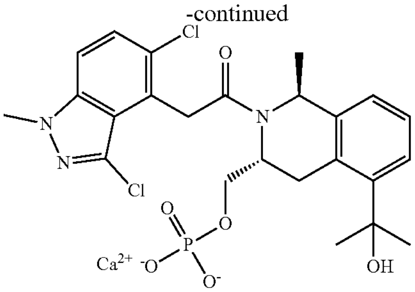

(II-A-Ca)

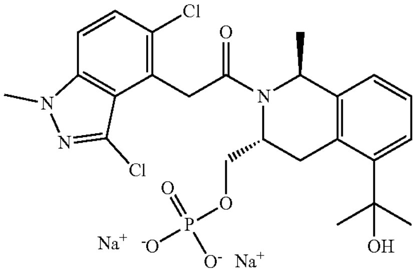

(II-A-Na)

3.1. Synthesis of Intermediate (a1)—dibenzyl [(1S,3R)-2-[2-(3,5-dichloro-1-methyl-indazol-4-yl)acetyl]-5-(1-hydroxy-1-methyl-ethyl)-1-methyl-3,4-dihydro-1H-isoquinolin-3-yl]methyl Phosphate To a suspension of (Ia) (10.0 g, 20.0 mmol) in DCM (210 mL) at rt was sequentially added dibenzyl n,n-diisopropylphosphoramidite (10.8 mL, 31.5 mmol), imidazole (1.43 g, 21.0 mmol) and imidazole hydrochloride (3.29 g, 31.5 mmol) and the reaction mixture was stirred at rt for 2 h. Then hydrogen peroxide (35% w/w in water, 10.4 mL, 128 mmol) was added in two portions over 45 min and the reaction mixture was stirred at rt for 1 h 30. The reaction mixture was then washed with a saturated sodium bisulphite solution (200 mL) and the aqueous phase was extracted with DCM twice. The combined organic phase was washed with brine, dried over $MgSO_4$ and concentrated in vacuo until dryness to give a pale-yellow oil. The crude product was purified by flash chromatography Biotage Isolera Four (100 g SFAR silica gel column in a gradient of Heptane:EtOAc 70:30 to 20:80 over 15 CV). The purest fractions were collected and the solvent was evaporated (30° C.) until dryness to afford dibenzyl [(1S,3R)-2-[2-(3,5-dichloro-1-methyl-indazol-4-yl)acetyl]-5-(1-hydroxy-1-methyl-ethyl)-1-methyl-3,4-dihydro-1H-isoquinolin-3-yl]methyl phosphate (a1) (11.9 g, 16.2 mmol, 81% yield) as a white solid.

Basic LCMS Method 1: 1 peak @ 1.71 min ($ES^+$): 758/760 $[M+Na]^+$, 458/460 $[M-(BnO)_2P(O)OH+H]^+$, 87% purity.

$^1H$ NMR (400 MHz, DMSO-$d_6$) δ 7.67 (dd, J=13.6, 9.0 Hz, 1H), 7.52 (dd, J=20.8, 9.0 Hz, 1H), 7.45-6.91 (m, 13H), 5.39 (d, J=6.7 Hz, 0.35H), 5.18-4.92 (m, 3.70H), 4.91-4.82 (m, 1.81H), 4.65 (m, 0.76H), 4.34 (dd, J=52.2, 16.5 Hz, 1.35H), 4.15-3.83 (m, 4.68H), 3.75 (dt, J=11.7, 6.2 Hz, 0.47H), 3.53 (q, J=9.0 Hz, 0.67H), 3.12 (m, 1.40H), 1.61-1.48 (m, 6.73H), 1.29-1.13 (m, 2.29H).

3.2. Synthesis of Compound (II-A)—[(1S,3R)-2-[2-(3,5-dichloro-1-methyl-indazol-4-yl)acetyl]-5-(1-hydroxy-1-methyl-ethyl)-1-methyl-3,4-dihydro-1H-isoquinolin-3-yl]methyl dihydrogen Phosphate In a glass Parr Reactor of 300 mL was introduced dibenzyl [(1S,3R)-2-[2-(3,5-dichloro-1-methyl-indazol-4-yl)acetyl]-5-(1-hydroxy-1-methyl-ethyl)-1-methyl-3,4-dihydro-1H-isoquinolin-3-yl]methyl phosphate (a1) (11.5 g, 15.6 mmol), THF (141 mL) and palladium (5% on carbon Paste JM type 87L, 764 mg, 0.359 mmol) and the reaction mixture was stirred under 4 bars of $H_2$ for 3 h. Then, the reaction mixture was filtered over a pad of celite and the filter cake was eluted with THF (200 mL). The filtrate was concentrated in vacuo until dryness to give a white solid. This crude mixture purified by reverse phase preparative HPLC GILSON basic mode (YMC Triart-500 g-10 μm-76.5×200 mm, Gradient elution ACN/(5 mL $NH_4OH$ in 1000 mL Water) 20/80 to 50/50). The purest fractions were collected and freeze-dried directly to afford a white solid. This white solid was purified a second time by reverse phase flash chromatography Biotage Isolera Four in acid conditions (by portions of 1.0 g, C18 SNAP 60 g gel column in a gradient from 20% to 50% ACN in water/formic acid (pH~5) over 12 CV). The purest fractions were collected and freeze-dried directly to afford [(1S,3R)-2-[2-(3,5-dichloro-1-methyl-indazol-4-yl)acetyl]-5-(1-hydroxy-1-methyl-ethyl)-1-methyl-3,4-dihydro-1H-isoquinolin-3-yl]methyl dihydrogen phosphate (II-A) (6.07 g, 10.9 mmol, 70% yield) as a white solid.

Basic LCMS Method 2: 1 peak @ 4.00 min ($ES^+$): 554/556 $[M-H]^-$, 97% purity.

Acid LCMS Method: 1 peak @ 2.30 min ($ES^+$): 554/556 $[M-H]^-$, 97% purity.

$^1H$ NMR (400 MHz, DMSO-$d_6$) δ 7.70-7.62 (m, 1H), 7.52 (t, J=8.7 Hz, 1H), 7.43-7.32 (m, 1H), 7.27-7.06 (m, 2H), 5.36 (d, J=6.8 Hz, 0.35H), 5.05 (q, J=6.5 Hz, 0.65H), 4.78-4.30 (m, 2.96H), 4.11 (dd, J=14.9, 6.0 Hz, 1.14H), 4.02 (s, 3.36H), 3.07 (m, 1.65H), 2.88 (m, 0.42H), 1.62-1.48 (m, 7.2H), 1.23 (d, J=6.4 Hz, 1.9H).

The crystallization of (II-A) was optimized using 100 mg of compound in 10 mL ethanol/pentane (10/1) solution. After 3 weeks, white crystals were obtained (20 mg, 20% yield). The scale-up of crystallization was performed on 700 mg divided in 5 batches of 140 mg using 10 mL ethanol/pentane (10/1). After 3 weeks, white crystals of [(1S,3R)-2-[2-(3,5-dichloro-1-methyl-indazol-4-yl)acetyl]-5-(1-hydroxy-1-methyl-ethyl)-1-methyl-3,4-dihydro-1H-isoquinolin-3-yl]methyl dihydrogen phosphate (II-Ax) were obtained (203 mg, 29% yield, combination of the 5 experiments).

3.3. Synthesis of Compound (II-A-Na)—disodium [(1S,3R)-2-[2-(3,5-dichloro-1-methyl-indazol-4-yl)acetyl]-5-(1-hydroxy-1-methyl-ethyl)-1-methyl-3,4-dihydro-1H-isoquinolin-3-yl]methyl Phosphate To a solution of [(1S,3R)-2-[2-(3,5-dichloro-1-methyl-indazol-4-yl)acetyl]-5-(1-hydroxy-1-methyl-ethyl)-1-methyl-3,4-dihydro-1H-isoquinolin-3-yl]methyl dihydrogen phosphate (II-A) (1.0 eq., 275 mg, 0.490 mmol) in water (0.1 M, 5 mL) at 0° C. was added a solution of sodium hydroxide (2.0 eq., 1 mL, 1 mmol, 1M solution) and the reaction was stirred at rt for 1 h. The reaction mixture was freeze dried overnight to afford disodium [(1S,3R)-2-[2-(3,5-dichloro-1-methyl-indazol-4-yl)acetyl]-5-(1-hydroxy-1-methyl-ethyl)-1-methyl-3,4-dihydro-1H-isoquinolin-3-yl]methyl phosphate (II-A-Na) (250 mg, 0.402 mmol, 82% yield) as a light-yellow solid.

$^1$H NMR (400 MHz, $D_2O$) δ 7.53-7.40 (m, 3H), 7.27 (m, 1H), 7.13 (d, J=7.4 Hz, 1H), 5.39 (s, 0.16H), 5.26 (d, J=6.8 Hz, 0.31H), 5.11 (q, J=6.5 Hz, 1H), 4.76 (d, J=9.4 Hz, 2H), 4.57 (d, J=17.5 Hz, 2H), 4.44-4.25 (m, 1H), 3.95 (d, J=4.1 Hz, 3H), 3.75-3.61 (m, 1H), 3.33-3.21 (m, 1H), 3.16 (d, J=14.1 Hz, 1H), 3.06 (d, J=15.9 Hz, 0.32H), 2.94-2.82 (m, 0.37H), 1.68 (d, J=3.5 Hz, 3H), 1.62 (d, J=6.7 Hz, 1H), 1.55 (d, J=9.4 Hz, 3H), 1.28 (d, J=6.6 Hz, 2H).

3.4. Synthesis of Compound (II-A-Ca)—calcium [(1S,3R)-2-[2-(3,5-dichloro-1-methyl-indazol-4-yl)acetyl]-5-(1-hydroxy-1-methyl-ethyl)-1-methyl-3,4-dihydro-1H-isoquinolin-3-yl]methyl Phosphate To a solution of [(1S,3R)-2-[2-(3,5-dichloro-1-methyl-indazol-4-yl)acetyl]-5-(1-hydroxy-1-methyl-ethyl)-1-methyl-3,4-dihydro-1H-isoquinolin-3-yl]methyl dihydrogen phosphate (II-A) (1.0 eq., 100 mg, 0.178 mmol) in water (0.1 M, 2 mL) at 0° C. was added calcium hydroxide (1.0 eq., 14 mg, 0.183 mmol) and the reaction was stirred at rt for 1 h. The reaction mixture was freeze dried overnight to afford calcium [(1S,3R)-2-[2-(3,5-dichloro-1-methyl-indazol-4-yl)acetyl]-5-(1-hydroxy-1-methyl-ethyl)-1-methyl-3,4-dihydro-1H-isoquinolin-3-yl]methyl phosphate (II-A-Ca) (110 mg, 0.179 mmol, 100% yield) as a white solid.

$^1$H NMR (400 MHz, $D_2O$) δ 7.49-7.37 (m, 3H), 7.22 (m, 1H), 7.10 (d, J=7.6 Hz, 1H), 5.35 (s, 0.10H), 5.28-5.21 (m, 0.58H), 5.07 (q, J=6.5 Hz, 1H), 4.52 (d, J=17.5 Hz, 2H), 4.44-4.25 (m, 1H), 3.95 (d, J=4.1 Hz, 3H), 3.75-3.61 (m, 1H), 3.33-3.21 (m, 1H), 3.16 (d, J=14.1 Hz, 1H), 3.06 (d, J=15.9 Hz, 0.32H), 2.94-2.82 (m, 0.37H), 1.68 (d, J=3.5 Hz, 3H), 1.62 (d, J=6.7 Hz, 1H), 1.55 (d, J=9.4 Hz, 3H), 1.28 (d, J=6.6 Hz, 2H).

4. Preparation of Compound (II-B)—[(1S,3R)-2-[2-(3,5-dichloro-1-methyl-indazol-4-yl)acetyl]-5-(1-hydroxy-1-methyl-ethyl)-1-methyl-3,4-dihydro-1H-isoquinolin-3-yl]methyl (2S)-2-amino-3-methyl-butanoate

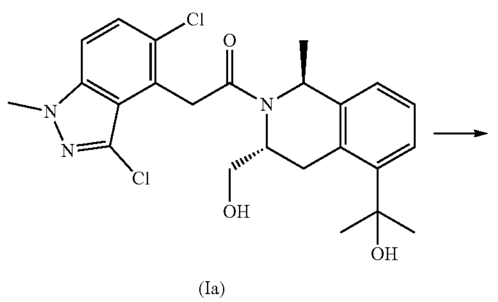

(Ia)

-continued

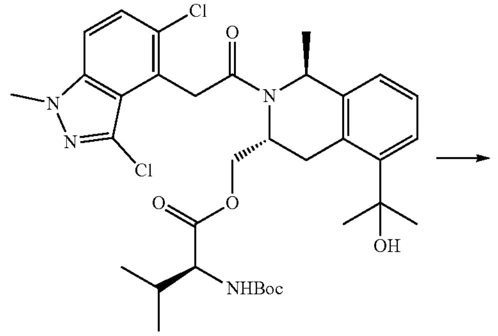

a2

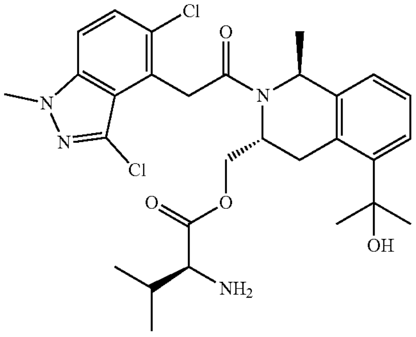

(II-B)

4.1. Synthesis of Intermediate (a2)—[(1S,3R)-2-[2-(3,5-dichloro-1-methyl-indazol-4-yl)acetyl]-5-(1-hydroxy-1-methyl-ethyl)-1-methyl-3,4-dihydro-1H-isoquinolin-3-yl]methyl (2S)-2-(tert-butoxycarbonylamino)-3-methyl-butanoate To a solution of (Ia) (8.00 g, 16.2 mmol) in DCM (170 mL) at rt was added (2S)-2-(tert-butoxycarbonylamino)-3-methyl-butanoic acid (Boc-L-Valine, 7.30 g, 33.2 mmol), DMAP (1.00 g, 8.40 mmol) and DCC (6.93 g, 33.6 mmol) and the mixture was stirred at rt for 18 h. Then, a saturated solution of $NaHCO_3$ was added and the aqueous layer was extracted with DCM (3 times). The combined organic layers were washed with brine, dried over $MgSO_4$, filtered and evaporated until dryness to give of a white solid. This crude mixture purified by reverse phase preparative HPLC GILSON basic mode (YMC Triart-500 g-10 μm-76.5×200 mm, Gradient elution ACN/(5 mL $NH_4OH$ in 1000 mL water) 60/40 to 90/10). The purest fractions were collected concentrated to dryness to afford [(1S,3R)-2-[2-(3,5-dichloro-1-methyl-indazol-4-yl)acetyl]-5-(1-hydroxy-1-methyl-ethyl)-1-methyl-3,4-dihydro-1H-isoquinolin-3-yl]methyl (2S)-2-(tert-butoxycarbonylamino)-3-methyl-butanoate (a2) (10.0 g, 14.8 mmol, 91% yield) as a white solid.

Basic LCMS Method 1: 1 peak @ 1.78 min ($ES^+$): 675/677 $[M+H]^+$, 575/577 $[M-Boc+H]^+$, 98% purity.

$^1$H NMR (400 MHz, DMSO-$d_6$) δ 7.67 (d, J=9.1 Hz, 1H), 7.53 (d, J=9.0 Hz, 1H), 7.44-7.33 (m, 1H), 7.28-7.02 (m, 2.45H), 6.87 (d, J=8.8 Hz, 0.35H), 5.39 (q, J=6.5 Hz, 0.38H), 5.23-4.85 (m, 1.50H), 4.83-4.35 (m, 2.93H), 4.19-3.73 (m, 5.64H), 3.72-3.43 (m, 2H), 3.20-3.12 (m, 1H), 1.97 (q, J=6.8 Hz, 0.53H), 1.71 (q, J=6.6 Hz, 0.49H), 1.62-1.46 (m, 7.45H), 1.35 (d, J=13.4 Hz, 9H), 1.25 (d, J=6.5 Hz, 2H), 0.82 (m, 4H), 0.69 (dd, J=18.2, 6.8 Hz, 2H).

4.2. Synthesis of Compound (II-B)—[(1S,3R)-2-[2-(3,5-dichloro-1-methyl-indazol-4-yl)acetyl]-5-(1-hydroxy-1-methyl-ethyl)-1-methyl-3,4-dihydro-1H-isoquinolin-3-yl]methyl (2S)-2-amino-3-methyl-butanoate To a solution of [(1S,3R)-2-[2-(3,5-dichloro-1-methyl-indazol-4-yl)acetyl]-5-(1-hydroxy-1-methyl-ethyl)-1-methyl-3,4-dihydro-1H-isoquinolin-3-yl]methyl (2S)-2-(tert-butoxycarbonylamino)-3-methyl-butanoate (a2) (10.0 g, 14.8 mmol) in 2-propanol (100 mL) at rt was added hydrochloric acid (37% in Water, 36.2 mL, 434 mmol) and the reaction mixture was stirred at rt for 30 min. To the resulting mixture were then added DCM and a saturated solution of $NaHCO_3$ until the pH reached 7-8 and the layers were separated. The aqueous layer was extracted with DCM twice. Then, the combined organic layers were dried over $MgSO_4$, filtered and concentrated to dryness to give a white solid. This crude mixture purified by reverse phase preparative HPLC GILSON basic mode (YMC Triart-500 g-10 μm-76.5×200 mm, Gradient elution ACN/(5 mL $NH_4OH$ in 1000 mL water) 50/50 to 100/0). The purest fractions were collected concentrated to dryness to afford the title product as white solid. The product was recrystallized in a mixture of EtOAc/pentane 5:2 (35 mL/g) to yield [(1S,3R)-2-[2-(3,5-dichloro-1-methyl-indazol-4-yl)acetyl]-5-(1-hydroxy-1-methyl-ethyl)-1-methyl-3,4-dihydro-1H-isoquinolin-3-yl]methyl (2S)-2-amino-3-methyl-butanoate (II-B) (3.30 g, 5.75 mmol, 39% yield) as white crystals.

Basic LCMS Method 2: 1 peak @ 4.59 min ($ES^+$): 575/577 $[M+H]^+$, 98% purity.

Acid LCMS Method: 1 peak @ 4.45 min ($ES^+$): 575/577 $[M+H]^+$, 99% purity.

$^1H$ NMR (400 MHz, DMSO-$d_6$) δ 7.67 (dd, J=9.1, 1.2 Hz, 1H), 7.53 (dd, J=9.0, 1.6 Hz, 1H), 7.36 (ddd, J=7.5, 5.4, 1.5 Hz, 1H), 7.28-7.07 (m, 2H), 5.40 (d, J=6.6 Hz, 0.43H), 5.07 (d, J=7.8 Hz, 1H), 5.00 (s, 0.41H), 4.77 (m, 0.58H), 4.70-4.35 (m, 2.26H), 4.20-3.81 (m, 5H), 3.51 (dd, J=11.1, 7.8 Hz, 0.56H), 3.42 (dd, J=10.3, 7.8 Hz, 0.45H), 3.20-3.07 (m, 1.38H), 2.78 (d, J=4.9 Hz, 0.41H), 1.82 (dq, J=13.2, 6.8 Hz, 0.44H), 1.70-1.35 (m, 9.31H), 1.24 (d, J=6.5 Hz, 1.62H), 0.85 (d, J=6.9 Hz, 1.81H), 0.77 (dd, J=6.8, 5.3 Hz, 3H), 0.66 (d, J=6.8 Hz, 1.46H).

5. Synthesis of Compound (II-C)—[(1S,3R)-2-[2-(3,5-dichloro-1-methyl-indazol-4-yl)acetyl]-5-(1-hydroxy-1-methyl-ethyl)-1-methyl-3,4-dihydro-1H-isoquinolin-3-yl]methyl (2S)-2-amino-4-methyl-pentanoate

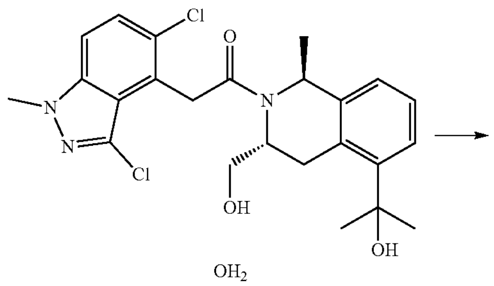

(Ia)

-continued

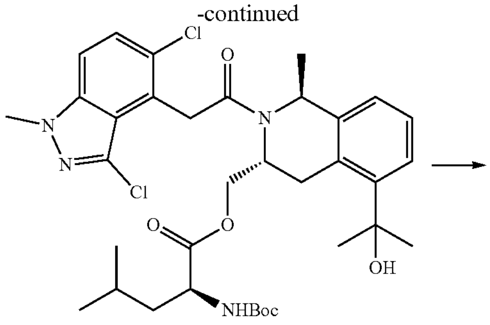

a3

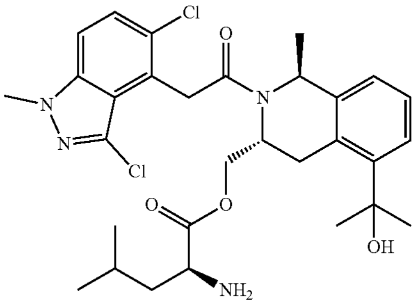

(II-C)

5.1. Synthesis of Intermediate (a3)—[(1S,3R)-2-[2-(3,5-dichloro-1-methyl-indazol-4-yl)acetyl]-5-(1-hydroxy-1-methyl-ethyl)-1-methyl-3,4-dihydro-1H-isoquinolin-3-yl]methyl (2S)-2-(tert-butoxycarbonylamino)-4-methyl-pentanoate To a suspension of (2S)-2-(tert-butoxycarbonylamino)-4-methyl-pentanoic acid (Boc-L-Leucine, 9.50 g, 40.3 mmol) and (Ia) (10.0 g, 20.2 mmol) in DCM (200 mL) at rt were added DMAP (1.24 g, 10.1 mmol) and DCC (8.35 g, 40.5 mmol) and the resulting reaction mixture was stirred at rt for 18 h. After LCMS monitoring showing incomplete conversion, extra DCC (2.09 g, 10.1 mmol) and (2S)-2,4-dimethylpentanoic acid (2.39 g, 10.1 mmol) were added to the reaction mixture and the resulting reaction mixture was stirred at rt for 20 h. After LCMS monitoring showing complete conversion, the reaction mixture was diluted with water and DCM and the layers were separated. The organic layer was washed with a saturated $NH_4Cl$ aqueous solution, a saturated $NaHCO_3$ aqueous solution, water, brine, dried over $Na_2SO_4$, filtered and concentrated to give a crude. The crude was purified by flash chromatography Biotage Isolera Four (solid loading on celite, 220 g SFAR silica gel in a gradient of Heptane/EtOAc 100/0 to 40/60). The fractions containing the desired compounds were collected and concentrated to give a residue which was then purified by flash chromatography Biotage Isolera Four (liquid loading in DCM, 220 g SFAR silica gel in a gradient of DCM/EtOAc 100/0 to 80/20). The fractions containing the desired product were combined and partially evaporated under reduced pressure until removal of all of the DCM to give a suspension which was filtered to give a solution which was concentrated to afford [(1S,3R)-2-[2-(3,5-dichloro-1-methyl-indazol-4-yl)acetyl]-5-(1-hydroxy-1-methyl-ethyl)-1-methyl-3,4-dihydro-1H-isoquinolin-3-yl]methyl (2S)-2-(tert-butoxycarbonylamino)-4-methyl-pentanoate (a3) (11.3 g, 16.4 mmol, 81% yield) as a white solid.

Basic LCMS Method 2: 1 peak @ 1.82 min ($ES^+$): 589 $[M+H-Boc]^+$, 98% purity.

Acid LCMS Method: 1 peak @ 1.82 min ($ES^+$): 589 $[M+H-Boc]^+$, 98% purity.

$^1$H NMR (400 MHz, $CDCl_3$) δ 7.42 (dd, J=9.0, 2.5 Hz, 1H), 7.35 (m, 1H), 7.24-7.16 (m, 2H), 7.07 (dd, J=16.3, 7.4 Hz, 1H), 5.27 (m, 1H), 4.86 (d, J=8.3 Hz, 0.5H), 4.83-4.78 (m, 0.5H), 4.71 (m, 0.5H), 4.67-4.52 (m, 2.5H), 4.43 (dd, J=11.1, 3.6 Hz, 0.5H), 4.38-4.23 (m, 1H), 4.21-4.15 (m, 0.5H), 4.10 (m, 0.5H), 3.98 (d, J=3.2 Hz, 3H), 3.65 (t, J=10.1 Hz, 0.5H), 3.45-3.26 (m, 1H), 3.16 (ddd, J=30.0, 16.1, 5.3 Hz, 1H), 1.82-1.46 (m, 10.5H), 1.42 (d, J=2.5 Hz, 9H), 1.38 (d, J=6.5 Hz, 1.5H), 0.91 (d, J=6.4 Hz, 3H), 0.82 (dd, J=10.8, 6.5 Hz, 3H).

5.2. Synthesis of Compound (II-C)—[(1S,3R)-2-[2-(3,5-dichloro-1-methyl-indazol-4-yl)acetyl]-5-(1-hydroxy-1-methyl-ethyl)-1-methyl-3,4-dihydro-1H-isoquinolin-3-yl]methyl (2S)-2-amino-4-methyl-pentanoate To a solution of [(1S,3R)-2-[2-(3,5-dichloro-1-methyl-indazol-4-yl)acetyl]-5-(1-hydroxy-1-methyl-ethyl)-1-methyl-3,4-dihydro-1H-isoquinolin-3-yl]methyl (2S)-2-(tert-butoxycarbonylamino)-4-methyl-pentanoate (a3) (10.0 g, 14.5 mmol) in 2-propanol (150 mL) at 0° C. was added hydrochloric acid (37% w/w in water, 36.2 mL, 434 mmol) and the reaction mixture was stirred from 4° C. to rt over 8 d. The reaction mixture was diluted with DCM (600 mL) before slow addition of a saturated $NaHCO_3$ aqueous solution until pH=8. The layers were separated, and the aqueous layer was extracted with DCM (2×400 mL). The combined organic layers were washed with a half saturated NaCl aqueous solution (800 mL), brine, dried over $Na_2SO_4$, filtered and concentrated to give a crude. The crude was purified twice by flash chromatography Biotage Isolera Four (liquid loading in DCM, 220 g SFAR silica gel in a gradient of Heptane/EtOAc/MeOH 50/50/0 to 0/100/0 then from 0/100/0 to 0/90/10) to give a white solid. The solids were dissolved in EtOAc (100 mL) and diluted with pentane (250 mL). The whole mixture was stirred at 35° C. for 30 min until obtention of a clear solution. The solution was allowed to cool down to rt and was stirred at 150 rpm at rt for 6 days to give a white suspension which was filtered. The solids were dried under high vacuum for 24 h at rt to afford [(1S,3R)-2-[2-(3,5-dichloro-1-methyl-indazol-4-yl)acetyl]-5-(1-hydroxy-1-methyl-ethyl)-1-methyl-3,4-dihydro-1H-isoquinolin-3-yl]methyl (2S)-2-amino-4-methyl-pentanoate (II-C) (2.56 g, 4.35 mmol, 30% yield) as white crystals.

Basic LCMS Method 2: 1 peak @ 4.80 min ($ES^+$): 589 $[M+H]^+$, 100% purity.

Acid LCMS Method: 1 peak @ 3.93 min ($ES^+$): 589 $[M+H]^+$, 100% purity.

$^1$H NMR (400 MHz, $CDCl_3$) δ 7.67 (d, J=9.0 Hz, 1H), 7.52 (dd, J=9.0, 1.4 Hz, 1H), 7.37 (ddd, J=8.0, 4.0, 1.5 Hz, 1H), 7.27-7.08 (m, 2H), 5.40 (q, J=6.5 Hz, 0.45H), 5.13-4.96 (m, 1.55H), 4.73 (dq, J=8.0, 3.9 Hz, 0.55H), 4.68-4.46 (m, 2H), 4.39 (d, J=16.7 Hz, 0.45H), 4.18 (dd, J=11.0, 4.6 Hz, 0.55H), 4.14-3.93 (m, 4H), 3.88 (dd, J=10.4, 2.9 Hz, 0.45H), 3.40 (ddd, J=18.2, 10.7, 8.4 Hz, 1H), 3.28 (m, 0.55H), 3.15 (dd, J=16.6, 4.7 Hz, 1H), 3.00 (dd, J=9.1, 5.3 Hz, 0.45H), 1.81-1.44 (m, 10H), 1.41-1.06 (m, 4H), 0.87-0.74 (m, 6H).

6. Solubility of Compounds of Formula (II-A), (II-Ax), (II-B) and (I)

The solubility of compounds of formula (Ia) obtained according to Example 2.12. and compounds of formula (II-A), (II-Ax) and (II-B) obtained respectively according to Examples 3.2. and 4.2., was determined in different media while using the shake flask method. An excess of solids, for (II-Ax) and (II-B) equivalent to a concentration of compound of formula (I) of 5 mg/mL, and for (II-A) equivalent to a concentration of compound of formula (I) of 1 mg/mL was suspended in 5 mL of buffer/biorelevant media as specifically described in Table 1 and incubated in a sealed glass vial (10 mL) for 24 h at room temperature or 37° C. (as indicated below) in a climatic chamber equipped with a rotary mixer. The 24 h time point was assumed to have reached solubility, at which time the suspension was filtered through a 0.45-μm ultra free filter (Merck Millipore) and the drug content was determined by HPLC. The solubility of compounds (Ia), (II-A), (II-Ax) and (II-B) was determined in triplicate (n=3) and mean value calculated.

The media tested are respectively water, phosphate buffer, FasSGF, FASSIF-V2 and FeSSIF-V2. FasSG is fasted condition gastric fluid. FasSGF is prepared at pH 1.6 and contains 0.08 mM Taurocholate, 0.02 mM phospholipids, 34 mM sodium and 59 mM chloride. FaSSIF-V2 and FeSSIF-V2 are Fasted and Fed State Biorelevant Media, respectively. FaSSIF-V2 is prepared at pH 6.5 and contains 3 mM Taurocholate, 0.2 mM Phospholipids, 106 mM Sodium, 69 mM Chloride and 19 mM Maleic acid. FeSSIF-V2 is prepared at pH 5.8 and contains 10 mM Taurocholate, 2 mM Phospholipids, 0.8 mM Oleate, 5 mM Glycerol monoleate, 218 mM Sodium, 125 mM Chloride and 55 mM Maleic acid.

TABLE 1

| | | Solubility Measurements (mean value)_(24 h) | | | |
|---|---|---|---|---|---|
| Media | pH/T° | Compound (Ia) | (II-A) | (II-Ax) | (II-B) |
| Water | 7.0/RT | <1 μg/mL | ~1000 μg/mL | / | ~40 μg/mL |
| Phosphate buffer (50 mM) | 4.0/RT | <1 μg/mL | ~1000 μg/mL | / | ~850 μg/mL |
| Phosphate buffer (50 mM) | 6.5/RT | <1 μg/mL | / | >5000 μg/mL | ~70 μg/mL |
| FasSGF | 1.6/37° C. | <1 μg/mL | / | / | ~4800 μg/mL |
| FaSSIF-V2 | 6.5/37° C. | ~1.5 μg/mL | ~1100 μg/mL | >5000 μg/mL | ~30 μg/mL |
| FeSSIF-V2 | 5.8/37° C. | ~4 μg/mL | ~1000 μg/mL | >5000 μg/mL | ~900 μg/mL |

The results obtained hereabove show that a minimum of 20-fold increase in solubility of prodrugs (II-A), (II-Ax) and (II-B) compared to compound of formula (Ia) is obtained, irrespective of the media used.

7. In Vivo Bioavailability of Suspensions of (II-A), (II-B) and (II-C)

7.1. Liquid Suspension of (II-A), (II-B) and (II-C)

The formulation vehicle used in the following suspension is a mixture of 1% (w/v) methylcellulose (400 cps), 0.1% (weight/volume) TWEEN® 80, 0.1% (w/v) Antifoam 1510 US in 25 mM phosphate buffer pH 3.0 in water.

Compound of formula (II) was weighed in the container of the ultrasonicator system (Covaris S220X) and formulation vehicle as described above was added, to achieve a concentration of compound of formula (II) of 0.72 g/ml.

The solution is homogenized by sonication during 1 minute, repeated 3 times.

7.2. Administration and Bioavailability Measurements

Three male Sprague-Dawley rats were administered the respective suspensions of (II-A), (II-B) and (II-C), as described in paragraph 7.1 above, at a single oral dose corresponding to 3 mg/kg of compound of formula (I).

Plasma samples were collected 0.12 h, 0.25 h, 0.5 h, 1 h, 2 h, 4 h and 8 h following dosing.

Plasma concentrations of compound (I) and respective compounds (II-A), (II-B) and (II-C) were quantified by LC/MS (liquid chromatography/mass spectrometry).

Figure 3:
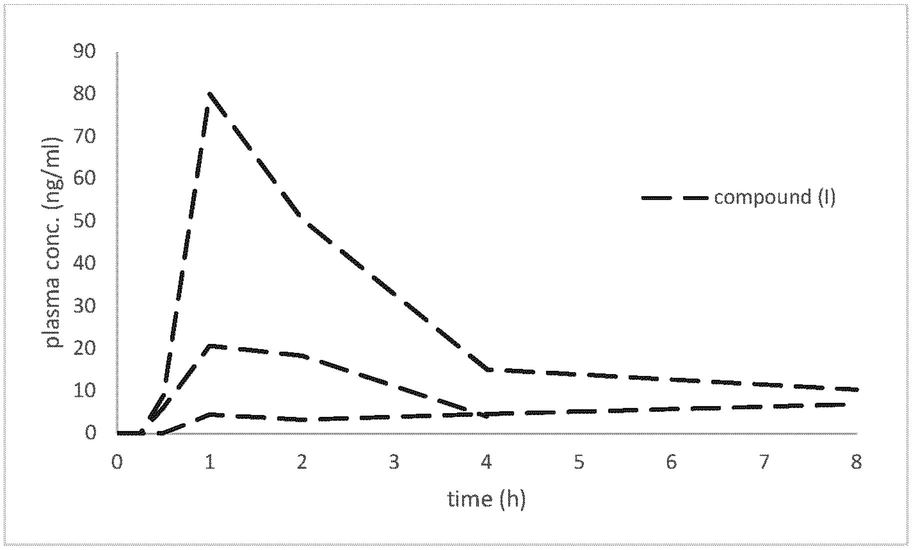
FIG. 3 represents a graph of the concentration of compound (I) in the plasma of three different animals plotted in function of time after administration of a suspension of prodrug (II-C) prepared according to Example 7 as further described herein.

FIGS. 1 and 3 show that all prodrugs (II-A) and (II-C) are completely cleaved into compound of formula (I) which circulates in the blood stream.

Figure 2:
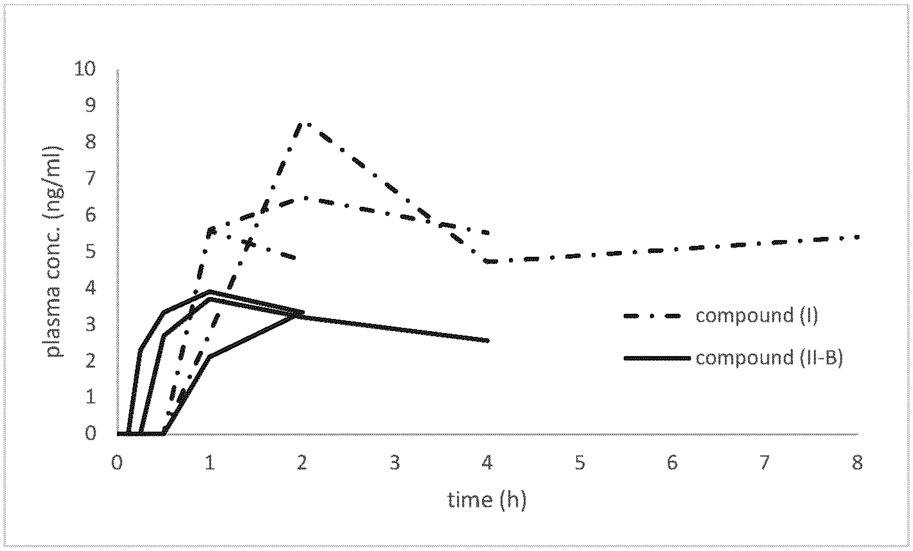
FIG. 2 represents a graph of the respective concentrations of compounds (I) and (II-B) in the plasma of three different animals plotted in function of time after administration of a suspension of prodrug (II-B) prepared according to Example 7 as further described herein.

FIG. 2 shows that prodrug (II-B) is partially cleaved into compound of formula (I).

The invention claimed is:

1. A compound of prodrug of formula (II), (II)

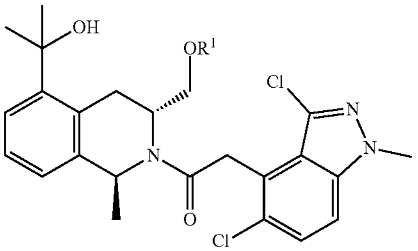

wherein $R^1$ represents —P(=O)(OH)$_2$, —P(=O)(OM$^1$)$_2$, —P(=O)(O$^-$)$_2$M$^2$ or —C(=O)R$^a$;

$R^a$ represents a $C_{1-6}$ alkyl substituted by amino;

$M^1$ represents a monovalent cation; and $M^2$ represents a divalent cation.

2. A compound of formula (II) according to claim 1 wherein $R^1$ represents —P(=O)(OH)$_2$.

3. A compound of formula (II) according to claim 1 wherein $R^a$ represents $C_{1-6}$ alkyl substituted by amino.

4. A compound of formula (II) according to claim 3 wherein $R^a$ represents (amino)butyl.

5. A compound of formula (II) according to claim 3 wherein $R^a$ represents (amino)pentyl.

6. A compound of formula (II) according to claim 1 which is selected from the group consisting of compounds represented by formula (II-A), (II-B) and (II-C), (II-A)

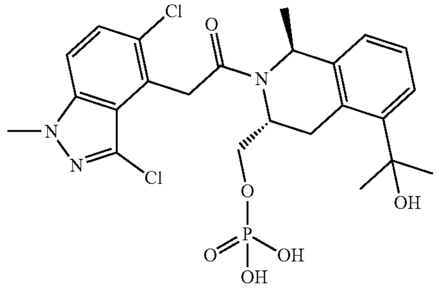

(II-B)

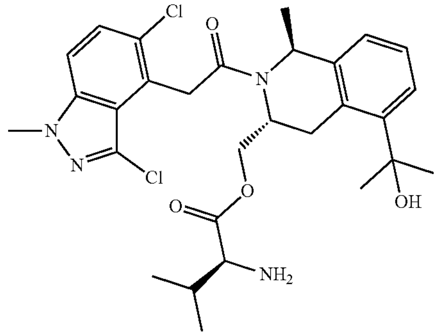

(II-C)

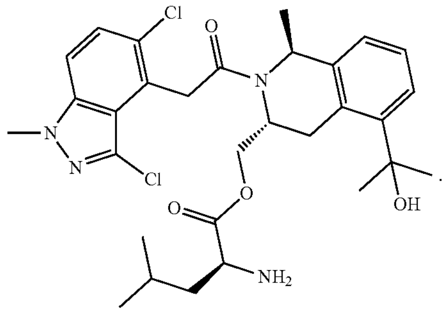

7. A compound of formula (II) according to claim 6 which is a compound of formula (II-A).

8. A compound of formula (II) according to claim 6 which is a compound of formula (II-B).

9. A compound of formula (II) according to claim 6 which is a compound of formula (II-C).

10. A compound of formula (II) according to claim 1 wherein $R^1$ represents P(=O)(OM$^1$)$_2$ or —P(=O)(O$^-$)$_2$M$^2$;

$M^1$ represents Na+; and $M^2$ represents Ca++.

11. A pharmaceutical composition comprising a compound of formula (II) according to claim 1 together with in association with a pharmaceutically acceptable diluent or carrier.

12. A method for the treatment of cognitive and negative symptoms in schizophrenia, cognitive impairment related to neuroleptic therapy, Mild Cognitive impairment (MCI), impulsivity, Attention-Deficit Hyperactivity Disorder (ADHD), Parkinson's disease and other movement disorders, dystonia, Parkinson's dementia, Huntington's disease, dementia with Lewy Body Alzheimer's , disease, drug addiction, sleep disorders, apathy, traumatic spinal cord injury or neuropathic pain, which comprises administering to a patient in need of such treatment an effective amount of a compound of formula (II) according to claim 1 or a pharmaceutical composition comprising a compound of formula (II) according to claim 1.

13. A compound which is converted in vivo to 2-(3,5-dichloro-1-methyl-indazol-4-yl)-1-[(1S,3R)-3-(hydroxymethyl)-5-(1-hydroxy-1-methyl-ethyl)-1-methyl-3,4-dihydro-1H-isoquinolin-2-yl]ethanone upon administration of the compound to a mammal, wherein the compound is represented by formula (II), (II)

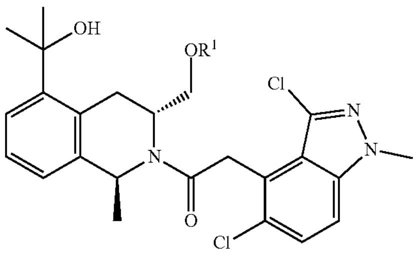

wherein $R^1$ represents —P(═O)(OH)$_2$, —P(═O)(OM$^1$)$_2$, —P(═O)(O$^-$)$_2$M$^2$ or —C(═O)R$^a$;

$R^a$ represents a $C_{1-6}$ alkyl substituted by amino;

$M^1$ represents a monovalent cation; and $M^2$ represents a divalent cation.

14. A compound of formula (II) according to claim 13 wherein $R^1$ represents P(═O)(OH)$_2$.

15. A compound of formula (II) according to claim 13 wherein $R^a$ represents $C_{1-6}$ alkyl substituted by amino.

16. A compound of formula (II) according to claim 15 wherein $R^a$ represents (amino)butyl.

17. A compound of formula (II) according to claim 15 wherein $R^a$ represents (amino)pentyl.

18. A compound of formula (II) according to claim 13 which is a compound of formula (II-A)

(II-A)

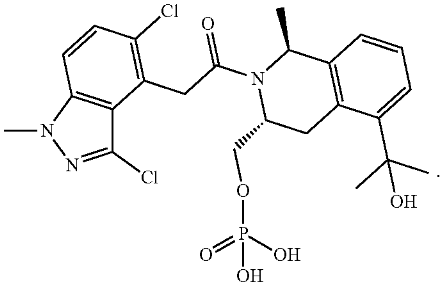

19. A compound of formula (II) according to claim 13 which is a compound of formula (II-B)

(II-B)

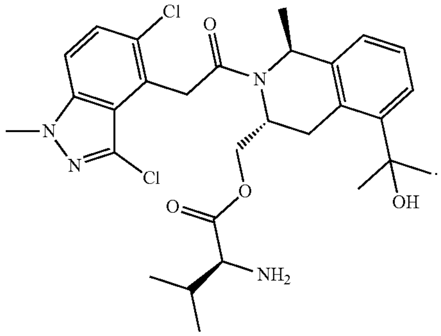

20. A compound of formula (II) according to claim 13 which is a compound of formula (II-C)

(II-C)

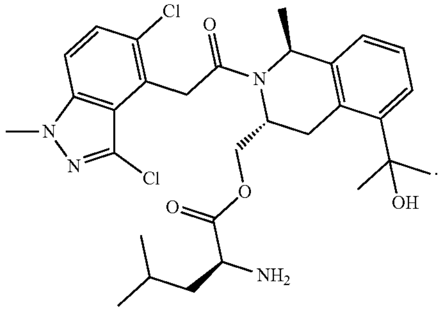

21. A compound of formula (II) according to claim 13 wherein $R^1$ represents P(═O)(OM$^1$)$_2$ or —P(═O)(O$^-$)$_2$M$^2$;

$M^1$ represents Na+; and $M^2$ represents Ca++.

22. Aa method for the treatment of cognitive and negative symptoms in schizophrenia, cognitive impairment related to neuroleptic therapy, Mild Cognitive impairment (MCI), impulsivity, Attention-Deficit Hyperactivity Disorder (ADHD), Parkinson's disease and other movement disorders, dystonia, Parkinson's dementia, Huntington's disease, dementia with Lewy Body, Alzheimer's disease, drug addiction, sleep disorders, apathy, traumatic spinal cord injury or neuropathic pain, which comprises administering to a patient in need of such treatment an effective amount of a compound of formula (II) according to claim 13 or a pharmaceutical composition comprising a compound of formula (II) according to claim 13.

* * * * *